United States Patent [19]

Ludmerer

[11] Patent Number: 5,952,216
[45] Date of Patent: Sep. 14, 1999

[54] SYNTHETIC HPV 16 VIRUS-LIKE PARTICLES

[75] Inventor: Steven Ludmerer, Piscataway, N.Y.

[73] Assignee: Merck & Co., Inc., Rahway, N.J.

[21] Appl. No.: 08/987,519

[22] Filed: Dec. 9, 1997

Related U.S. Application Data

[60] Provisional application No. 60/032,633, Dec. 9, 1996.

[51] Int. Cl.[6] .............................. C12N 7/00; C12N 7/01; C12Q 1/70
[52] U.S. Cl. ........................... 435/235.1; 435/7.1; 435/5; 435/7.92; 435/69.3; 424/204.1
[58] Field of Search ............................... 435/69.3, 235.1, 435/7.1, 5, 7.92; 424/204.1

[56] References Cited

U.S. PATENT DOCUMENTS 5,437,951  8/1995  Lowy et al. ........................ 435/69.1

OTHER PUBLICATIONS

Pakula et al. Annu Review of Genet (United States), 1989, vol. 23, pp. 289–310. (abstract only).

Park et al, 1993, Journal of Virological Method, vol. 45, pp. 303–318.

Kimbauer, R. et al., "Efficient Self–Assembly of Human Papillomavirus Type 16 L1 and L1–L2 into Virus–Like Particles", J. Virology, vol. 67, pp. 6929–6936, 1993.

Yamada, T. et al, "Human Papillomavirus Type 16 Variant Lineages in United States Populations . . .", J. Virology, vol. 69, No. 12, pp. 7743–7753, 1995.

Roden, R. B. et al, "Assessment of the Serological Relatedness of Genital Human Papillomaviruses by Hemagglutination Inhibition" J. Virology, vol. 70, No. 5, pp. 3298–3301, 1996.

Sigma Immuno Chemicals, P. No. A7784, A9688, A8062, 1994.

*Primary Examiner*—Mary E. Mosher
*Assistant Examiner*—Ali R Salimi
*Attorney, Agent, or Firm*—Joanne M. Giesser; Jack L. Tribble

[57] ABSTRACT

A series of synthetic virus-like particles useful in the characterization of human papillomavirus type 16 (HPV16) infection and assays employing the synthetic particles are provided.

1 Claim, 1 Drawing Sheet

```
HPV11     --------------------------------------------------Y--KV------------   4
HPV6b     --------------------------------------------------F--RA------------   4

Consensus MWRPSDSTVYVPPPNPVSKVVATDAYV-RTNIFYHASSSRLLAVGHPY-SIK--NKTVVPKVSGYQYRVFKVVLPDPNKFALPDSSLFDPTTQRLVWACT 100

HPV11     -------------------------------L------GY----------------T-S-S-N---  11
HPV6b     -------------------------------F------S-----------------K-T-P-A---  10

Consensus GLEVGRGQPLGVGVSGHP-LNKYDDVENSG--GGNPGQDNRVNVGMDYKQTQLCMVGCAPPLGEHWGKG-QC-NT-VQ-GDCPPLELITSVIQDGDMVDT 200

HPV11     -------------L-----------V-------------Y------------T------D-LV--GN-S--A-----H---  23
HPV6b     -------------I-----------T-------------F------------E------T-II--SG-T--G-----N---  22

Consensus GFGAMNFADLQTNKSDVP-DICGT-CKYPDYLQMAADPYGDRLFF-LRKEQMFARHFFNRAG-VGEPVPD-L--KG--NR-SV-SSIYV-TPSGSLVSSE 300

HPV11     -----------------------------H-----------------SK-A-------F-------------  28
HPV6b     -----------------------------Q-----------------TT-S-------Y-------------  27

Consensus AQLFNKPYWLQKAQGHNNGICWGN-LFVTVVDTTRSTNMTLCASV--S-TYTNSDYKEYMRHVEE-DLQFIFQLCSITLSAEVMAYIHTMNPSVLEDWNF 400

HPV11     ---------------------Q----DM----------------------F---------T-A--I-----P-T---T---  38
HPV6b     ---------------------P----NL----------------------Y---------S-I--V-----A-A---A---  37

Consensus GLSPPPNGTLEDTYRYVQSQAITCQKPTEKEK-DPYK--SFWEVNLKEKFSSELDQ-PLGRKFLLQSGYRGR-S-RTG-KRPAVSK-S-APKRKR-KTK 500

HPV11     K   39
HPV6b     R   38

Consensus -   501
```

FIG.1

SEQUENCE LISTING

<160> NUMBER OF SEQ ID NOS: 3

<210> SEQ ID NO 1
<211> LENGTH: 500
<212> TYPE: PRT
<213> ORGANISM: Human Papillomavirus

<400> SEQUENCE: 1

```
Met Trp Arg Pro Ser Asp Ser Thr Val Tyr Val Pro Pro Asn Pro
 1               5                  10                  15

Val Ser Lys Val Val Ala Thr Asp Ala Tyr Val Lys Arg Thr Asn Ile
                20                  25                  30

Phe Tyr His Ala Ser Ser Ser Arg Leu Leu Ala Val Gly His Pro Tyr
             35                  40                  45

Tyr Ser Ile Lys Lys Val Asn Lys Thr Val Pro Lys Val Ser Gly
     50                  55                  60

Tyr Gln Tyr Arg Val Phe Lys Val Val Leu Pro Asp Pro Asn Lys Phe
 65                  70                  75                  80

Ala Leu Pro Asp Ser Ser Leu Phe Asp Pro Thr Thr Gln Arg Leu Val
                 85                  90                  95

Trp Ala Cys Thr Gly Leu Glu Val Gly Arg Gly Gln Pro Leu Gly Val
                100                 105                 110

Gly Val Ser Gly His Pro Leu Leu Asn Lys Tyr Asp Asp Val Glu Asn
                115                 120                 125

Ser Gly Gly Tyr Gly Gly Asn Pro Gly Gln Asp Asn Arg Val Asn Val
        130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
                180                 185                 190

Gln Asp Gly Asp Met Val Asp Thr Gly Phe Gly Ala Met Asn Phe Ala
            195                 200                 205

Asp Leu Gln Thr Asn Lys Ser Asp Val Pro Leu Asp Ile Cys Gly Thr
        210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
                340                 345                 350

Asn Ser Tyr Lys Glu Tyr Met Arg His Val Glu Glu Phe Asp Leu Gln
        355                 360                 365
```

-continued

```
Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
                420                 425                 430

Gln Asp Pro Tyr Lys Asp Met Ser Phe Trp Glu Val Asn Leu Lys Glu
            435                 440                 445

Lys Phe Ser Ser Glu Leu Asp Gln Phe Pro Leu Gly Arg Lys Phe Leu
    450                 455                 460

Leu Gln Ser Gly Tyr Arg Gly Arg Thr Ser Ala Arg Thr Gly Ile Lys
465                 470                 475                 480

Arg Pro Ala Val Ser Lys Pro Ser Thr Ala Pro Lys Arg Lys Arg Thr
                485                 490                 495

Lys Thr Lys Lys
            500

<210> SEQ ID NO 2
<211> LENGTH: 500
<212> TYPE: PRT
<213> ORGANISM: Human Papillomavirus

<400> SEQUENCE: 2

Met Trp Arg Pro Ser Asp Ser Thr Val Tyr Val Pro Pro Asn Pro
1               5                   10                  15

Val Ser Lys Val Ala Thr Asp Ala Tyr Val Thr Arg Thr Asn Ile Phe
                20                  25                  30

Tyr His Ala Ser Ser Ser Arg Leu Leu Ala Val Gly His Pro Tyr Phe
            35                  40                  45

Ser Ile Lys Arg Ala Asn Lys Thr Val Val Pro Lys Val Ser Gly Tyr
    50                  55                  60

Gln Tyr Arg Val Phe Lys Val Val Leu Pro Asp Pro Asn Lys Phe Ala
65                  70                  75                  80

Leu Pro Asp Ser Ser Leu Phe Asp Pro Thr Thr Gln Arg Leu Val Trp
                85                  90                  95

Ala Cys Thr Gly Leu Glu Val Gly Arg Gly Gln Pro Leu Gly Val Gly
                100                 105                 110

Val Ser Gly His Pro Phe Leu Asn Lys Tyr Asp Asp Val Glu Asn Ser
            115                 120                 125

Gly Ser Gly Gly Asn Pro Gly Gln Asp Asn Arg Val Asn Val Gly Met
    130                 135                 140

Asp Tyr Lys Gln Thr Gln Leu Cys Met Val Gly Cys Ala Pro Pro Leu
145                 150                 155                 160

Gly Glu His Trp Gly Lys Gly Lys Gln Cys Thr Asn Thr Pro Val Gln
                165                 170                 175

Ala Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240
```

```
Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Ala Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Ser Ser Thr Tyr Thr Asn
                340                 345                 350

Ser Asp Tyr Lys Glu Tyr Met Arg His Val Glu Glu Tyr Asp Leu Gln
            355                 360                 365

Phe Ile Phe Gln Leu Cys Ser Ile Thr Leu Ser Ala Glu Val Met Ala
370                 375                 380

Tyr Ile His Thr Met Asn Pro Ser Val Leu Glu Asp Trp Asn Phe Gly
385                 390                 395                 400

Leu Ser Pro Pro Asn Gly Thr Leu Glu Asp Thr Tyr Arg Thr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
            435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Arg Ser Ser Ile Arg Thr Gly Val Lys
465                 470                 475                 480

Arg Pro Ala Val Ser Lys Ala Ser Ala Ala Pro Lys Arg Lys Arg Ala
            485                 490                 495

Lys Thr Lys Arg
            500

<210> SEQ ID NO 3
<211> LENGTH: 501
<212> TYPE: PRT
<213> ORGANISM: Artificial Sequence
<220> FEATURE:
<221> NAME/KEY: SIMILAR
<222> LOCATION: (0)...(0)
<223> OTHER INFORMATION: Consensus Sequence
<223> OTHER INFORMATION: At 28 X = K or T
      At  49 X = Y or F
      At  53 X = K or R
      At  54 X = V or A
      At 119 X = L or F
      At 131 X = G or S
      At 132 X = Y or No Residue
      At 170 X = T or K
      At 173 X = S or T
      At 176 X = S or P
      At 179 X = N or A
      At 219 X = L or I
      At 225 X = V or T
      At 246 X = Y or F
      At 263 X = T or E
      At 271 X = D or T
      At 273 X = L or I
      At 274 X = V or I
      At 277 X = G or S
```

```
At 278 X = N or G
At 281 X = S or T
At 284 X = A or G
At 290 X = H or N
At 325 X = H or Q
At 346 X = S or T
At 347 X = K or T
At 348 X = A or S
At 366 X = F or Y
At 434 X = Q or P
At 439 X = D or N
At 440 X = M or L
At 458 X = F or Y
At 474 X = T or S
At 476 X = A or I
At 480 X = I or V
At 488 X = P or A
At 490 X = T or A
At 497 X = T or A
At 501 X = K or R
```

<400> SEQUENCE: 3

```
Met Trp Arg Pro Ser Asp Ser Thr Val Tyr Val Pro Pro Asn Pro
 1               5                  10                  15

Val Ser Lys Val Val Ala Thr Asp Ala Tyr Val Xaa Arg Thr Asn Ile
            20                  25                  30

Phe Tyr His Ala Ser Ser Ser Arg Leu Leu Ala Val Gly His Pro Tyr
            35                  40                  45

Xaa Ser Ile Lys Xaa Xaa Asn Lys Thr Val Pro Lys Val Ser Gly
50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
                100                 105                 110

Gly Val Ser Gly His Pro Xaa Leu Asn Lys Tyr Asp Asp Val Glu Asn
                115                 120                 125

Ser Gly Xaa Xaa Gly Gly Asn Pro Gly Gln Asp Asn Arg Val Asn Val
                130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Xaa Gln Cys Xaa Asn Thr Xaa
                165                 170                 175

Val Gln Xaa Gly Asp Cys Pro Pro Leu Glu Leu Ile Thr Ser Val Ile
                180                 185                 190

Gln Asp Gly Asp Met Val Asp Thr Gly Phe Gly Ala Met Asn Phe Ala
                195                 200                 205

Asp Leu Gln Thr Asn Lys Ser Asp Val Pro Xaa Asp Ile Cys Gly Thr
                210                 215                 220

Xaa Cys Lys Tyr Pro Asp Tyr Leu Gln Met Ala Ala Asp Pro Tyr Gly
225                 230                 235                 240

Asp Arg Leu Phe Phe Xaa Leu Arg Lys Glu Gln Met Phe Ala Arg His
                245                 250                 255

Phe Phe Asn Arg Ala Gly Xaa Val Gly Glu Pro Val Pro Asp Xaa Leu
                260                 265                 270

Xaa Xaa Lys Gly Xaa Xaa Asn Arg Xaa Ser Val Xaa Ser Ser Ile Tyr
                275                 280                 285

Val Xaa Thr Pro Ser Gly Ser Leu Val Ser Ser Glu Ala Gln Leu Phe
                290                 295                 300
```

```
Asn Lys Pro Tyr Trp Leu Gln Lys Ala Gln Gly His Asn Asn Gly Ile
305                 310                 315                 320

Cys Trp Gly Asn Xaa Leu Phe Val Thr Val Val Asp Thr Thr Arg Ser
                325                 330                 335

Thr Asn Met Thr Leu Cys Ala Ser Val Xaa Xaa Ser Xaa Thr Tyr Thr
            340                 345             350

Asn Ser Asp Tyr Lys Glu Tyr Met Arg His Val Glu Glu Xaa Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Xaa Asp Pro Tyr Lys Xaa Xaa Ser Phe Trp Glu Val Asn Leu Lys
        435                 440                 445

Glu Lys Glu Ser Ser Glu Leu Asp Gln Xaa Pro Leu Gly Arg Lys Phe
        450                 455                 460

Leu Leu Gln Ser Gly Tyr Arg Gly Arg Xaa Ser Xaa Arg Thr Gly Xaa
465                 470                 475                 480

Lys Arg Pro Ala Val Ser Lys Xaa Ser Xaa Ala Pro Lys Arg Lys Arg
                485                 490                 495

Xaa Lys Thr Lys Xaa
                500
```

SYNTHETIC HPV 16 VIRUS-LIKE PARTICLES

CROSS-REFERENCE TO RELATED APPLICATIONS

This application claims the benefit of the provisional U.S. application Ser. No. 60/032,633 filed Dec. 9, 1996.

FIELD OF THE INVENTION

A series of synthetic virus-like particles useful in the characterization of human papillomavirus type 16 (HPV16) infection and assays employing the synthetic particles are provided.

BACKGROUND OF THE INVENTION

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. Papillomaviruses are species specific infective agents; a human papillomavirus cannot infect a nonhuman animal.

Papillomaviruses may be classified into distinct groups based on the host that they infect. Human papillomaviruses (HPV) are further classified into more than 60 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital or respiratory mucosa. HPV types 16 and 18 cause epithelial dysplasia of the genital mucosa and are associated with the majority of in situ and invasive carcinomas of the cervix, vagina, vulva and anal canal. HPV6 and HPV11 are the causative agents for more than 90% of all condyloma (genital warts) and laryngeal papillomas. The most abundant subtype of HPV type 6 is HPV6a.

Immunological studies in animals have shown that the production of neutralizing antibodies to papillomavirus antigens prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model. Neutralization of papillomavirus by antibodies appears to be type-specific and dependent upon conformational epitopes on the surface of the virus.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and cellular transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis. Immunologic data suggest that most of the L2 protein is internal to the L1 protein. The L2 proteins are highly conserved among different papillomaviruses, especially the 10 basic amino acids at the C-terminus. The L1 ORF is highly conserved among different papillomaviruses.

The L1 and L2 genes have been used to generate vaccines for the prevention and treatment of papillomavirus infections in animals. Zhou et al., (1991; 1992) cloned HPV type 16 L1 and L2 genes into a vaccinia virus vector and infected CV-1 mammalian cells with the recombinant vector to produce virus-like particles (VLP).

Bacterially-derived recombinant bovine papillomavirus L1 and L2 have been generated. Neutralizing sera to the recombinant bacterial proteins cross-reacted with native virus at low levels, presumably due to differences in the conformations of the native and bacterially-derived proteins.

Recombinant baculoviruses expressing HPV6 L1, HPV11 L1, HPV16 L1, HPV18 L1, HPV31 L1 or HPV16 L2 ORFs have been used to infect insect Sf9 cells and produce L1 and L2 proteins. Western blot analyses showed that the baculovirus-derived L1 and L2 proteins reacted with antibody to HPV16. The baculovirus derived L1 forms VLPs.

Carter et al., (1991) demonstrated the production of HPV 16 L1 and HPV16 L2 proteins by recombinant strains of *Saccharomyces cerevisiae*. Carter et al. also demonstrated the production of HPV6b L1 and L2 proteins. The HPV6b L1 protein was not full-length L1 protein. The recombinant proteins were produced as intracellular as well as secreted products. The recombinant L1 and L2 proteins were of molecular weights similar to the native proteins. When the proteins were expressed intracellularly, the majority of the protein was found to be insoluble when the cells were lysed in the absence of denaturing reagents. Although this insolubility may facilitate purification of the protein, it may hamper analysis of the native epitopes of the protein.

Recombinant proteins secreted from yeast were shown to contain yeast-derived carbohydrates. The presence of these N-linked oligosaccharides may mask native epitopes. In addition, the secreted recombinant proteins may contain other modifications, such as retention of the secretory leader sequence.

The present invention is directed to the production of recombinant papillomavirus proteins having the immunity-conferring properties of the native papillomavirus proteins as well as methods for their production and use. The present invention is a series of synthetic virus-like particles useful in the characterization of human papillomavirus infection and assays employing the synthetic virus-like particles.

The invention is an HPV16 L1 gene with E substituted for the naturally occurring D at L1 residue 202. This gene produces VLPs in baculovirus transfected Sf9 cells which bind MAb H16.U4, but not MAb H16.V5. These two MAbs are both been demonstrated both by competition and mutant binding studies to represent two distinct classes of HPV16 specific, VLP dependent Mabs. To date, all other HPV16-specific, VLP-dependent MAbs have been observed to be of one of the same two classes of antibodies.

The panel of neutralizing monoclonal antibodies for HPV16 was obtained from Neil Christensen (Pennsylvania State University, Hershey, Pa.). The monoclonal antibodies in the panel are all type-specific and VLP-dependent. The antibodies may be distinguished from each other in terms of which amino acid residues affect binding of the individual antibodies, although there are overlapping positions for all the monoclonal antibodies. Additional antibodies used in these studies were also obtained from Dr. Neil Christensen.

The HPV16:D202E substituted gene produces VLPs as judged by non-compromised binding of MAb H16.U4. This MAb is HPV16 specific and VLP dependent. HPV16:D202E VLPs do have compromised binding to H16:V5, also an HPV16 specific, VLP dependent MAb shown both by us and by Dr. Neil Christensen to bind VLPs in a distinctly different manner from H16:U4. These VLPs can be useful to distinguish and characterize immunological responses to HPV16 infection or vaccination.

This problem has not been solved in the past and, to our knowledge, is the first demonstration that a conformationally dependent epitope is continuous.

There was a major difficulty to overcome. The epitope is conformational so it was necessary to express any test L1 protein in a way that facilitated formation of virus-like particles which mimic the virus structure.

Without isolation of a type-specific epitope, it would be difficult to discriminate HPV16 responses.

One use of the derivatized HPV16 VLP is as a reagent in a serological assay. Test sera can be assayed for binding to HPV16:D202E VLPs. Binding demonstrates the presence of a U4 type-response. It can also be used to assess the relative levels of V5 type-responses among different sera samples.

SUMMARY OF THE INVENTION

A series of synthetic virus-like particles useful in the characterization of human papillomavirus type 16 (HPV16) infection and assays employing the synthetic particles are provided.

BRIEF DESCRIPTION OF THE DRAWINGS

FIG. 1 shows the amino acid sequences of HPV16 L1 protein in the region mutagenized, and also shows the specific substitutions made in this study. These sequences are also available in the EMBL Gene Bank.

DETAILED DESCRIPTION OF THE INVENTION

A series of synthetic virus-like particles useful in the characterization of human papillomavirus type 16 (HPV16) infection and assays employing the synthetic particles are provided. The synthetic VLPs may be used to monitor serological responses to HPV16 infection and immunization.

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection.

Papillomaviruses may be classified into distinct groups based on the host that they infect. Human papillomaviruses (HPV) are further classified into more than 60 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital and respiratory mucosa. HPV types 16 and 18 cause epithelial dysplasia of the genital tract and are associated with the majority of in situ and invasive carcinomas of the cervix, vagina, vulva and anal canal. HPV6 and HPV11 cause the majority of genital warts and laryngeal papillomas.

Immunological studies in animals have shown that the production of neutralizing antibodies to papillomavirus capsid proteins prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model. Neutralization of papillomavirus by antibodies appears to be type-specific and dependent upon conformational epitopes on the surface of the virus.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where “E” denotes early and “L” denotes late. L1 and L2 code for virus capsid proteins. The early (E) genes are associated with functions such as viral replication and transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis.

The production of HPV 16 L1, HPV16 L2, and HPV6 L1 proteins by recombinant strains of *Saccharomyces cerevisiae* has been reported. It would be useful to develop methods of producing large quantities of papillomavirus proteins of any species and type by cultivation of recombinant yeasts. It would also be useful to produce large quantities of papillomavirus proteins having the immunity-conferring properties of the native proteins, such as the conformation of the native protein. To achieve this latter goal it would be necessary to analyze the effect of numerous mutations in the L1 gene on the binding of antibodies of known properties (VLP dependent, cross-reactive, etc.)

The empirical scanning of natural or engineered peptide sequences for functional residues is inherently dependent upon expression of large numbers of sequence variants to assay their relative functional potency. The level of protein expression obtained can be particularly critical in the case of self-assembling viral structural proteins, because the efficiency of self-assembly frequently is concentration dependent. The insect baculovirus expression vector system has been widely used to study viral self-assembly, but it generally requires prior isolation and expansion of a plaque-purified recombinant viral stock to generate useful quantities of self-assembled particles. In examining a number of possibilities for expression of analytical levels of the L1 coat protein of Cottontail Rabbit and Human Type 11 Papillomaviruses, we found that even brief transient cotransfection of insect cells with baculovirus transfer vectors and viral DNA yielded assembled particles which were immunologically indistinguishable from particles previously obtained from plaque purified stocks (Benincasa et. al. 1996. Rapid, high-level transient expression of papillomavirus-like particles in insect cells. *BioTechniques* 20,890–895). Within six days of plasmid/viral DNA cotransfection of Sf9 cells, at least 1–2 μg of assembled L1 particles/100 mm plate could be demonstrated. This level of expression is more than sufficient to assay functionality, and has several advantages over comparable mammalian cell transient expression systems.

To define neutralizing epitopes in HPV infections, we needed to identify the amino acid residues that confer antigenic type-specificity on human papillomavirus subtypes (Christensen, N. D., et. al. 1990, Monoclonal antibody-mediated neutralization of infectious human papillomavirus type 11). Many of the type-specific epitopes are conformationally-dependent and are detectable only upon VLP assembly. The L1 structural coat protein of several animal and human papillomaviruses has been demonstrated to efficiently self-assemble when expressed in insect cells via recombinant baculovirus strains (Christensen, N. D., et al., 1994, Assembled baculovirus-expressed human papillomavirus type 11 L1 capsid protein virus-like particles are recognized by neutralizing monoclonal antibodies and induce high titers of neutralizing antibodies. J. Gen. Virol. 75, 2271–2276). The time and labor involved in the generation of recombinant phage precludes the use of this method to screen a large number of VLP variants produced through site-directed mutagenesis. However, we previously observed that when expressed in the baculovirus system, a recombinant protein is detectable as a secreted product in μg/ml quantities within 5–7 days of the initial transfection of insect cells with plasmid and viral DNAs. Based upon this observation, we examined whether sufficient quantities of papillomavirus L1 protein would accumulate to allow self-assembly into VLPs upon transient expression, particularly if a more efficient baculovirus transfection system such as the Baculogold™ (Pharmingen, San Diego, Calif.) system were utilized. Employing a rapid 6-day transient transfection protocol, the L1 coat protein of numerous papillomavirus types, properly assembled into VLPs, was produced. Extracts prepared from transiently transfected cells with CRPV or HPV11 L1 gene constructs contained immunogenic material recognized by type-specific and VLP dependent monoclonal antibodies generated against either CRPV or HPV11 VLPs. The transiently expressed material was not cross-reactive with other type-specific antibodies, and recognition was sensitive to alkaline denaturation, further demonstrating fidelity in VLP formation.

We previously demonstrated that conformational epitopes to HPV can be mapped. Specifically, we showed that HPV11 L1 residues $Gly^{131}$-$Tyr^{132}$ as responsible for the type-specific binding of several HPV11 neutralizing monoclonal antibodies (Ludmerer et. al. 1996. Two amino acid residues confer type specificity to a neutralizing, conformationally dependent epitope on human papillomavirus type 11. *J. Virol.* 70, 4791–4794). To assess affects on HPV16 residue 202 substitutions, we mutated the HPV16 L1 gene at this position, and employed the Sf9 transient expression system described above to express VLPs.

The following examples are provided to further define the invention without, however, limiting the invention to the particulars of these examples.

EXAMPLE 1
Generation of Test Expression Constructs.

The HPV16 L1 structural gene was subcloned both into BluScript (Pharmacia) for mutagenesis, and pVL1393 (Stratagene) for expression in Sf9 cells. Mutations were generated using the Amersham Sculptor in vitro mutagenesis kit, verified by sequencing, and subcloned into pVL1393 for expression in Sf9 cells.

EXAMPLE 2
Transient Expression of L1 VLPs in SF9 Cells.

SF9 cells were transfected using BaculoGold Transfection kit (Pharmingen). Transfections were done essentially according to the manufacturer's instructions with the following modifications. $8 \cdot 10^8$ Sf9 cells were transfected in a 100 mM dish, with 4 μg of BaculoGold DNA and 6 μg of test DNA. Cells were harvested after 6 days and assayed for VLP production.

EXAMPLE 3
Preparation of SF9 Extracts and ELISA Assays.

Cells were harvested six days after transfection, by scraping followed by low speed centrifugation. Cells were resuspended in 300 μl of breaking buffer (1 M NaCl, 0.2 M Tris pH 7.6) and homogenized for 30" on ice using a Polytron PT 1200 B with a PT-DA 1205/2-A probe (Brinkman) in a Falcon 1259 tube. Samples were spun at 2500 rpm for 3 minutes to pellet debris. Tubes were washed with an additional 150 μl of breaking buffer, supernatants collected in a 1.5 ml microfuge tube, and respun for 5 minutes in an Eppendorf microfuge (Brinkman). Supernatants were collected and stored at 4° C. until use. ELISA assays typically were performed the same day.

5 μl of extract was diluted into 50 μl of 1% BSA in PBS (phosphate buffered saline; 20 mM $NaPO_4$, pH 7.0, 150 mM NaCl) and plated onto a polystyrene plate. The plate was incubated overnight at 4° C. Extracts were removed and the plate blocked with 5% powdered milk in PBS. All subsequent wash steps were performed with 1% BSA in PBS. The plate was incubated at room temperature with primary antibody for 1 hour. Primary antibodies, monoclonal antibodies generated against HPV11 VLPs, were obtained as ascites stock from Dr. Neil Christensen (Pennsylvania State University). They were diluted $10^5$ in 1% BSA PBS before use. After washing, plates were incubated for 1 hour with secondary antibody. The secondary antibody, peroxidase labeled Goat anti-Mouse IgG (γ), was purchased from Kirkegaard & Perry Laboratories, Inc. and used at $10^3$ dilution in 1% BSA in PBS. After a final washing, an alkaline phosphatase assay was performed and absorbance read at 405 nm.

EXAMPLE 4
HPV16 Substitutions

To assess affects on Mab binding to HPV16 L1 substitutions, we expressed mutated clones transiently in Sf9 cells and assayed binding in an ELISA format to extracts prepared from transfected cells. L1 expression was normalized using MAb H16.D9, a MAb generated against HPV16 VLPs which binds only denatured material. To establish a baseline of MAb binding, we also expressed clone HPV16:D202H, an L1 clone previously demonstrated to not produce VLPs. As a further control, we also expressed HPV11 VLPs. MAbs H16.U4 and H16.V5 do not bind HPV11 VLPs.

To determine the affect on binding of any particular residue, both HPV16 and the correspondent HPV16 derivative were expressed in the transient expression system. An ELISA was performed using the panel of HPV16 specific monoclonal antibodies, and results between the two compared. L1 production was normalized with monoclonal antibody H16.D9. H61.D9 antibody is cross-reactive with HPV11, and its epitope is linear and recognized independently of VLP formation. Thus it measures L1 production. A normalized value in the range of 0.1 to 0.2 is essentially background, meaning we cannot detect binding of the antibody to the mutant VLP.

TABLE 1

| VLP | H16.U4 | H16.V5 |
|---|---|---|
| HPV16 | 0.79 | 1.08 |
| HPV16:D202E | 0.59 | 0.15 |
| HPV16:D202H | 0.21 | 0.19 |
| HPV11 | 0.06 | 0.06 |

EXAMPLE 5

Monitoring Serological Responses to HPV11 Infection or Immunization

HPV16:D202E VLPs are used to monitor immune responses to HPV16 following viral infection or immunization with HPV16 VLPs. HPV16 and HPV16:D202E will be coated onto the well of a microtiter plate in native form. Following blocking, test sera will be incubated and assayed in ELISA format. Binding to HPV16:D202E VLPs will demonstrate a U$4-like component to the immune response. To determine a V5 type response, test sera will first be equilibrated with a pre-determined saturating amount of HPV16:D202E VLPs. This can be performed in the well of a microtiter plate. The supernatant will be removed and added as primary antibody to the well of a microtiter plate pre-coated with HPV16 prototype VLPs. Because U4-like responses will have been selectively removed, binding will demonstrate the presence of V5-like responses.

EXAMPLE 6

Transient Expression of VLPs in Sf9 Cells

The HPV11 L1 structural gene was cloned from clinical isolates using the Polymerase Chain Reaction (PCR) with primers designed from the published L1 sequence (8,17). The CRPV L1 structural gene was cloned by PCR from viral genomic DNA. The L1 genes were subcloned into pVL1393 (Stratagene) for expression in Sf9 cells.

Sf9 cells were cotransfected using the BaculoGold Transfection kit (Pharmingen, San Diego, Calif.). Transfections were done according to the manufacturer's instructions with the following modification: $8 \cdot 10^6$ Sf9 cells were transfected in a 100 mm dish, with 4 μg of BaculoGold viral DNA and 6 ug of test plasmid DNA. Cells were harvested after 6 days, except where otherwise specified, and assayed for VLP production by Western Blot or ELISA assay (below).

EXAMPLE 7

Preparation of Sf9 Extracts and ELISA Assays

Cells were harvested six days after transfection. Plates were scraped to resuspend cells, and the cells were collected by low speed centrifugation. Cells were resuspended in 300 μl of breaking buffer (1 M NaCl, 0.2 M Tris pH 7.6) and homogenized for 30 seconds on ice using a Polytron PT 1200 B with a PT-DA 1205/2-A probe (Brinkman) in a Falcon 2059 tube. Samples were spun at 2500 rpm in a GPR centrifuge (Beckman Instruments, Inc. Palo Alto, Calif.) for 3 minutes to pellet debris. Tubes were washed with an additional 150 μl of breaking buffer, supernatants collected in a 1.5 ml microfuge tube, and respun for 5 minutes in an Eppendorf microfuge (Brinkman). ELISA assays were begun the same day.

5 μl of extract was diluted into 50 μl of 1% BSA in phosphate-buffered saline solution (PBS), aliquoted onto a 96 well Immulon 2 microtiter plate (Dynatech Laboratories, Inc.), and incubated overnight at 4° C. Extracts were removed and the plate blocked with 5% powdered milk/PBS. All subsequent wash steps were performed with 1% BSA/PBS. The plate was incubated at room temperature with primary antibody for 1 hour. The primary antibodies, monoclonal antibodies CRPV.5A and H11.F1, were obtained as ascites stock from Dr. Neil Christensen. They are VLP-dependent and type specific antibodies which recognize CRPV and HPV11 VLPs respectively (Neil Christiansen, personal communication). They were diluted $10^5$-fold in 1% BSA/PBS before use. After washing in 1% BSA/PBS, plates were incubated for 1 hour with secondary antibody, peroxidase labeled Goat anti-Mouse IgG (g) (Kirkegaard & Perry Laboratories, Inc.) and used at $10^3$ dilution in 1% BSA in PBS. After a final washing, an alkaline phosphatase assay was performed and absorbance read at 405 nm.

What is claimed:

1. A synthetic human papillomavirus virus-like particle designated HPV16D202E, wherein amino acid residue 202 is glutamate, not aspartic acid.

* * * * *